US011559626B2

(12) United States Patent
Bodner (10) Patent No.: US 11,559,626 B2
(45) Date of Patent: Jan. 24, 2023

(54) MEANS TO TREAT ALZHEIMER'S DISEASE VIA FLUSHING OF BRAIN PARENCHYMA

(71) Applicant: Medtronic, Inc., Minneapolis, MN (US)

(72) Inventor: Jeffrey P. Bodner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 339 days.

(21) Appl. No.: 16/843,367

(22) Filed: Apr. 8, 2020

(65) Prior Publication Data
US 2021/0316069 A1   Oct. 14, 2021

(51) Int. Cl.
*A61M 5/142*  (2006.01)
*A61M 5/172*  (2006.01)

(52) U.S. Cl.
CPC ...... *A61M 5/1723* (2013.01); *A61M 5/14276* (2013.01); *A61M 2202/0464* (2013.01); *A61M 2205/3331* (2013.01); *A61M 2205/50* (2013.01); *A61M 2210/0693* (2013.01); *A61M 2210/1003* (2013.01); *A61M 2230/06* (2013.01); *A61M 2230/40* (2013.01); *A61M 2230/50* (2013.01); *A61M 2230/62* (2013.01); *A61M 2230/63* (2013.01)

(58) Field of Classification Search
CPC .. A61M 2202/0464; A61M 2210/0693; A61M 2210/1003; A61M 5/14276
See application file for complete search history.

(56) References Cited

U.S. PATENT DOCUMENTS

| 6,945,969 B1 * | 9/2005 | Morris | A61M 5/14276 604/93.01 |
|---|---|---|---|
| 7,341,577 B2 | 3/2008 | Gill | |
| 7,963,956 B2 * | 6/2011 | Kunst | A61M 39/04 604/93.01 |
| 8,332,038 B2 * | 12/2012 | Heruth | A61B 5/4809 607/45 |
| 10,874,798 B2 * | 12/2020 | Wostyn | A61K 38/193 |

(Continued)

FOREIGN PATENT DOCUMENTS

| CA | 2393221 A1 * | 6/2007 |
| WO | WO03/015710 A2 | 2/2003 |

(Continued)

OTHER PUBLICATIONS

PCT International Search Report and Written Opinion corresponding to PCT/US2021/026326 dated Jun. 22, 2021.

*Primary Examiner* — Laura A Bouchelle
(74) *Attorney, Agent, or Firm* — Patterson Thuente (57) ABSTRACT

An implantable glymphatic pump configured to flush metabolites from a brain parenchyma of a patient. The implantable glymphatic pump including at least one spinal catheter having a distal end configured to be positioned within an intrathecal space of a spine of a patient, at least one cranial catheter having a distal end configured to be positioned within a brain parenchyma of the patient, and an implantable pump configured to draw cerebrospinal fluid from the intrathecal space of the spine in the patient via the at least one spinal catheter, and reintroduce said cerebrospinal fluid to the brain parenchyma of the patient via the one or more cranial catheters to encourage a flow of the cerebrospinal fluid through the brain parenchyma.

31 Claims, 10 Drawing Sheets

(56) References Cited

U.S. PATENT DOCUMENTS

| | | | |
|---|---|---|---|
| 2005/0038371 A1* | 2/2005 | Reich | A61M 39/24 |
| | | | 604/9 |
| 2010/0030196 A1* | 2/2010 | Hildebrand | A61M 27/006 |
| | | | 604/540 |
| 2016/0000945 A1 | 1/2016 | Nedergaard et al. | |
| 2019/0009014 A1* | 1/2019 | Chen | C07K 16/18 |

FOREIGN PATENT DOCUMENTS

| WO | WO2015/049588 A2 | 4/2015 |
|---|---|---|
| WO | WO2016/059162 A1 | 4/2016 |

* cited by examiner

MEANS TO TREAT ALZHEIMER'S DISEASE VIA FLUSHING OF BRAIN PARENCHYMA

TECHNICAL FIELD

The present technology is generally related to treating patients with neurodegenerative diseases, and more particularly to systems and methods for flushing the brain parenchyma of a patient.

BACKGROUND

The human brain includes compartments for four types of fluid: cerebrospinal fluid (CSF), interstitial fluid, intracellular fluid, and blood. CSF has a total volume of between about 150 and about 160 mL, which makes up about 10% of the total volume of fluid within the cranial cavity. The brain produces about 500 mL of CSF per day, such that the entire volume of CSF is renewed between about 4-12 times over the course of 24 hours. The volume of CSF within the cranial cavity at any given time is kept constant by circulation and removal of the CSF through the central nervous system.

During circulation, a portion of CSF penetrates the brain parenchyma, where the CSF flows through the spaces between cells. The porous structure of the parenchyma provides a low resistance pathway for influx of CSF. The parenchymal tissue is not believed to absorb any CSF, but simply provides one of several pathways enabling a general flow of CSF fluid to the subarachnoid space.

The physiological system enabling a flow of CSF through the brain parenchyma, where the CSF is interchanged with the interstitial fluid, is commonly referred to as the "glymphatic system." It is believed that the glymphatic system promotes a natural flushing of interstitial solutes from the parenchyma. Clearance of interstitial solutes from the parenchyma is believed to be of particular importance in the prevention of neurodegenerative diseases.

SUMMARY OF THE DISCLOSURE

The techniques of this disclosure generally relate to implantable pump systems and methods configured to encourage a flow of CSF through the glymphatic system for the purpose of flushing the brain parenchyma of metabolites to reduce or slow an accumulation of interstitial solute buildup in patients suffering from early stages of neurodegenerative diseases.

Accordingly, embodiments of the present disclosure address potential reductions in efficiency of biological glymphatic systems to naturally flush themselves of metabolites by using an implantable glymphatic pump to draw cerebrospinal fluid from a first location (e.g., from the intrathecal space of a patient's spine) and reintroduce said cerebrospinal fluid to a second location (e.g., the parenchymal tissue of a patient's brain) via one or more cranial catheters to enhance a natural flow of the cerebrospinal fluid within the biological glymphatic system of the patient. Thereafter, the cerebrospinal fluid can naturally flow through the brain parenchyma, eventually making its way back to the intrathecal space of a patient's spine. In some embodiments it is contemplated that the glymphatic pump can additionally introduce an infusate (e.g., brain parenchyma porosity relaxing medicament, cleansing saline solution, etc.) along with the reintroduced cerebrospinal fluid. In other embodiments, the implantable pump is configured to solely encourage a flow of cerebrospinal fluid from the intrathecal space to the brain parenchyma, and therefore is less likely to result in hydrocephalus. In embodiments without a reservoir, the implantable pump can have a smaller displacement in comparison to conventional implantable pump mechanisms.

In some embodiments, embodiments of the present disclosure can be configured to primarily operate during a patient's sleep. In some embodiments, embodiments of the present disclosure can further include various physiological sensors (e.g., a heart rate sensor, respiration sensor, inclination sensor, one or more accelerometers, temperature sensor, etc.), as an aid in confirming that a patient is asleep. As a safety mechanism, embodiments of the present disclosure can further include one or more pressure sensors configured to infer when a flow of the cerebrospinal fluid may be too aggressive for a current porosity of the parenchymal tissue. To ensure patient safety, the glymphatic pump can reduce the flow rate of cerebrospinal fluid based on feedback from the one or more pressure sensors.

One embodiment of the present disclosure provides an implantable glymphatic pump, including at least one spinal catheter, at least one intraparenchymal catheter and an implantable pump. The at least one spinal catheter can have a distal end configured to be positioned within an intrathecal space of a spine of a patient. The at least one intraparenchymal catheter can have a distal end configured to be positioned within a parenchymal tissue of the patient. The implantable pump can be configured to draw cerebrospinal fluid from the intrathecal space of the spine in the patient via the at least one spinal catheter, and reintroduce said cerebrospinal fluid to the parenchymal tissue of the patient via the one or more cranial catheters to encourage a flow of the cerebrospinal fluid through the parenchymal tissue.

In one embodiment, the at least one cranial catheter can include a first intraparenchymal catheter configured to be positioned in a right hemisphere of a brain of the patient and a second intraparenchymal catheter configured to be positioned in a left hemisphere of the brain of the patient. In one embodiment, the implantable pump can include at least one of a peristaltic pump, diaphragm pump, piston pump, rotor pump, or screw pump. In one embodiment, the implantable pump can occupy a total volume of about 60 cc or less. In one embodiment, the implantable pump can include a fluid reservoir. In one embodiment, the implantable pump can be configured to mix an infusate contained in the fluid reservoir with cerebrospinal fluid for introduction into the parenchymal tissue of the patient via the one or more intraparenchymal catheters.

In one embodiment, the implantable pump can include at least one physiological sensor configured to aid in a determination of a preferred operating time of the implantable pump. In one embodiment, a preferred operating time of the implantable pump can occur during a sleep state of the patient. In one embodiment, the at least one physiological sensor can be at least one of a heart rate sensor, respiratory sensor, inclination sensor, accelerometer, or temperature sensor. In one embodiment, the implantable pump can include a pressure sensor configured to sense a back pressure of cerebrospinal fluid reintroduced into the parenchymal tissue. In one embodiment, the implantable pump can further include a processor configured to use data sensed by the pressure sensor to infer a porosity of the parenchymal tissue as an aid in regulating a flow rate of the implantable pump.

Another embodiment of the present disclosure provides an implantable glymphatic pump, which can include at least one spinal catheter, at least one cranial catheter and an implantable pump. The at least one spinal catheter can have a distal end configured to be positioned within an intrathecal space of a spine of a patient. The at least one cranial catheter can have a distal end distal end configured to be positioned within a cranial cavity of the patient. The implantable pump can be configured to draw cerebrospinal fluid from the intrathecal space of the spine in the patient via the at least one spinal catheter, and reintroduce said cerebrospinal fluid to the cranial cavity of the patient via the one or more cranial catheters to encourage a flow of the cerebrospinal fluid through parenchymal tissue of the patient, wherein the implantable pump includes at least one physiological sensor configured to aid in a determination of a preferred operating time of the implantable pump.

Another embodiment of the present disclosure provides an implantable glymphatic pump, which can include at least one spinal catheter, at least one cranial catheter and an implantable pump. The at least one spinal catheter having a distal end can be configured to be positioned within an intrathecal space of a spine of a patient. The at least one cranial catheter can have a distal end configured to be positioned within a cranial cavity of the patient. The implantable pump can be configured to draw cerebrospinal fluid from the intrathecal space of the spine in the patient via the at least one spinal catheter, and reintroduce said cerebrospinal fluid to the cranial cavity of the patient via the one or more cranial catheters to encourage a flow of the cerebrospinal fluid through parenchymal tissue of the patient, wherein the implantable pump includes a pressure sensor configured to sense a back pressure of cerebrospinal fluid reintroduced into the cranial cavity.

Another embodiment of the present disclosure provides a method of aiding a glymphatic system of a patient, including: drawing cerebrospinal fluid from an intrathecal space of a spine of a patient; pumping said cerebrospinal fluid through an implantable pump; and reintroducing said cerebrospinal fluid into parenchymal tissue of the patient to encourage a flow of cerebrospinal fluid through the parenchymal tissue as an aid in flushing metabolites from the parenchymal tissue of the patient.

The details of one or more aspects of the disclosure are set forth in the accompanying drawings and the description below. Other features, objects, and advantages of the techniques described in this disclosure will be apparent from the description in the drawings, and from the claims.

BRIEF DESCRIPTION OF THE DRAWINGS

The disclosure can be more completely understood in consideration of the following detailed description of various embodiments of the disclosure, in connection with the accompanying drawings, in which.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Figure 1:
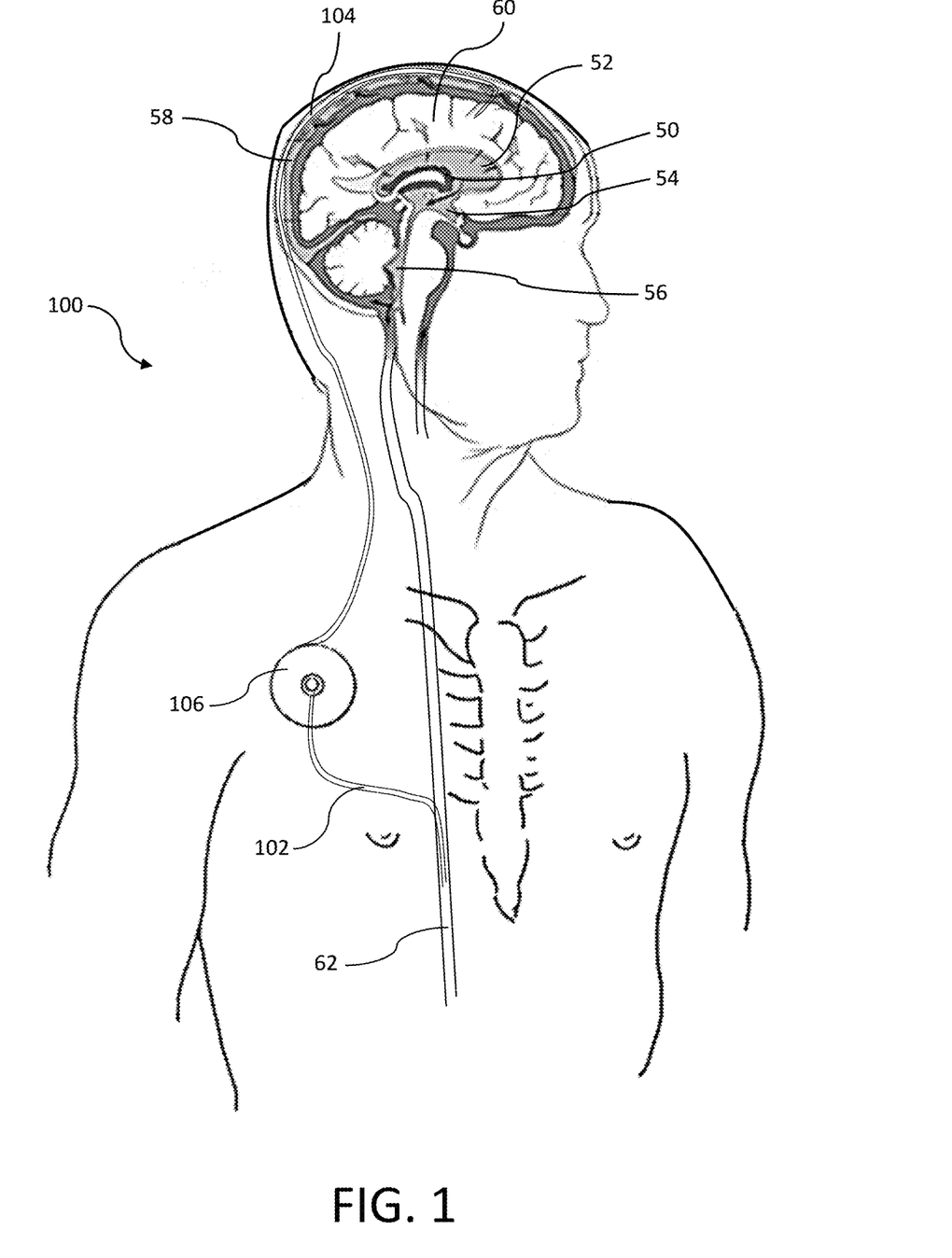
FIG. 1 depicts an implantable glymphatic pump implanted within a body of the patient, in accordance with an embodiment of the disclosure.

Referring to FIG. 1, an implantable glymphatic pump 100 configured to draw cerebrospinal fluid (CSF) from an intrathecal space of a patient and reintroduce said CSF into the intracranial cavity of the patient for the purpose of flushing metabolites from brain parenchyma, is depicted in accordance with an embodiment of the disclosure. In some embodiments, the implantable glymphatic pump 100 can include at least one spinal catheter 102, at least one cranial catheter 104, and an implantable pump 106.

CSF is formed within ventricles of the brain by small, delicate tufts of tissue referred to as choroid plexuses 50 lining the lateral ventricle 52, third ventricle 54 and fourth ventricle 56. CSF circulates through the central nervous system in a general flow from the lateral ventricle 52, to the third ventricle 54, the fourth ventricle 56, and into the subarachnoid space 58 surrounding the brain and spinal cord 62, where it eventually drains into the lymphatic system. The flow of CSF is thought to be primarily driven by a combination of arterial pulsatility, respiration and CSF pressure gradients. During circulation, a portion of CSF penetrates the brain parenchyma 60, where the CSF flows through the spaces between cells. The porous structure of the parenchyma tissue provides a low resistance pathway for influx of CSF. The parenchymal tissue is not believed to absorb any CSF, but simply provides one of several pathways enabling a general flow of CSF fluid to the subarachnoid space 58.

The physiological system enabling a flow of CSF through the parenchymal tissue, where it is interchanged with the interstitial fluid, is commonly referred to as the "glymphatic system." Recent research has revealed that neurotic plaque formation and neurofibrillary tangle accumulation in the brain is the result of a reduction in efficiency of the glymphatic system. In particular, a poor flow of CSF through the glymphatic system may result in a gradual accumulation of toxic dysfunctional proteins in the central nervous system, which in turn is commonly associated with diseases such as Alzheimer's disease, Parkinson's disease, Huntington's disease, and amyotrophic lateral sclerosis (ALS). Accordingly, it is believed that poor glymphatic clearance can contribute to a buildup of amyloid plaque (e.g., β-amyloid) and tau tangles (e.g., intracellular neurofibrillary tangles), two hallmarks of Alzheimer's disease. Further, it is believed that glymphatic activity is dramatically enhanced during sleep, as the porosity of the brain parenchyma naturally opens up between about 20-50%. Conversely, it is believed that the function of the glymphatic system is generally suppressed during wakefulness.

In other words, one physiological function of sleep appears to be an increase in glymphatic activity to naturally flush the brain parenchyma of neurotoxic waste, which offers a potential explanation for the apparent connection between sleep disorders and neurological diseases, such as Alzheimer's disease. The accumulation of amyloid plaque (e.g., β-amyloid) and tau tangles (e.g., intracellular neurofibrillary tangles), are two hallmarks of Alzheimer's disease. Accordingly, mounting evidence that Alzheimer's disease may be a disease of fluid mechanics opens the door to potential success from device-based therapy options.

Figure 2:
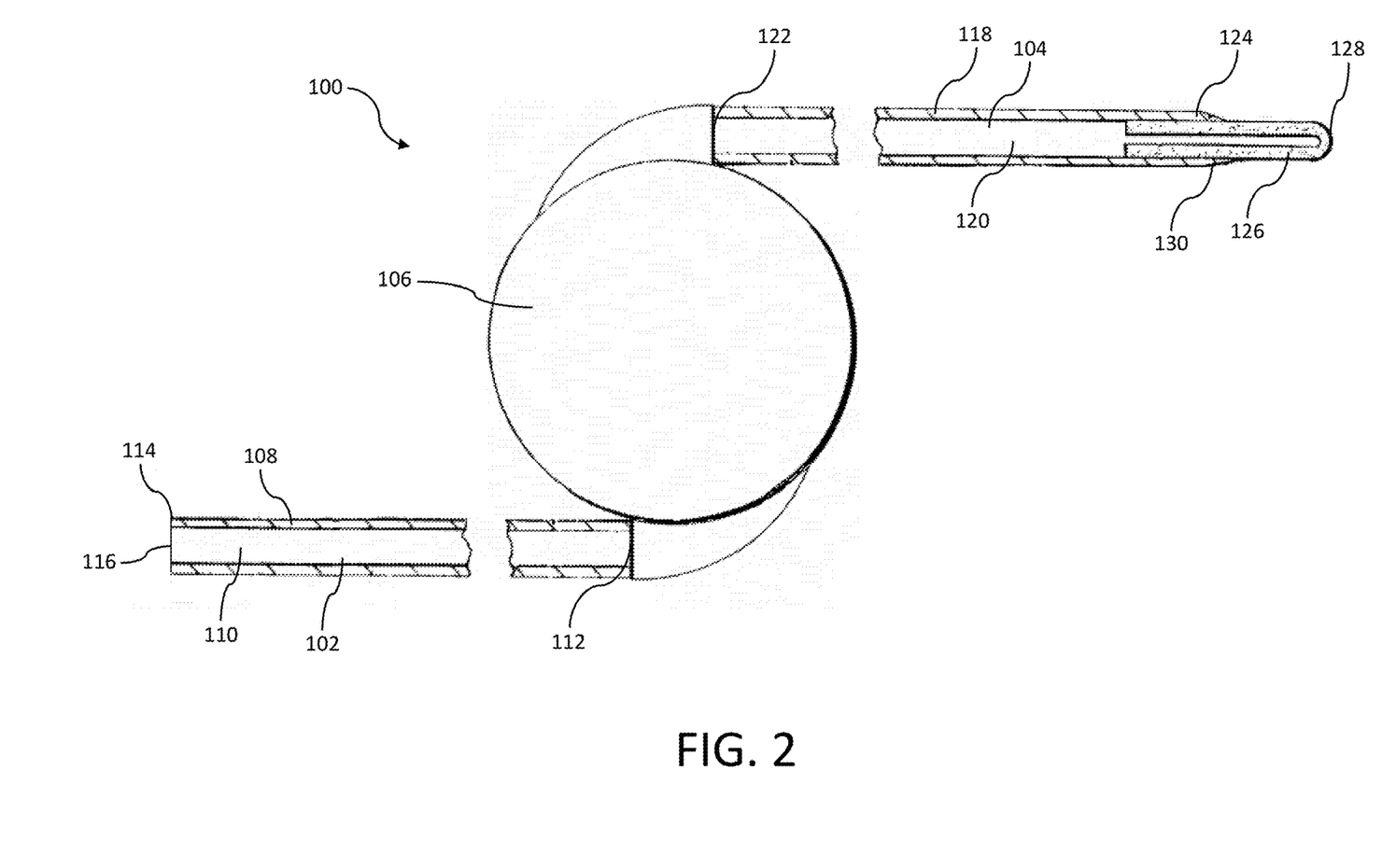
FIG. 2 depicts an implantable glymphatic pump configured to augment a natural function of a biological glymphatic system in flushing metabolites from parenchyma tissue, in accordance with an embodiment of the disclosure.

With additional reference to FIG. 2, an implantable glymphatic pump 100 including a spinal catheter 102, cranial catheter 104 and an implantable pump 106 configured to augment the natural function of a biological glymphatic system in flushing metabolites from parenchymal tissue is depicted in accordance with an embodiment of the disclosure. For example, in one embodiment, the implantable pump 106 is configured to draw CSF from the intrathecal space of the spine in the patient via at least one spinal catheter 102, and reintroduce said CSF to the parenchymal tissue of the patient via the at least one cranial catheter 104 to encourage a flow of the CSF through the parenchymal tissue. In encouraging a flow of CSF through the parenchymal tissue, the implantable pump 106 helps or stimulates the natural biological function of the glymphatic a system by actively introducing a flow of pressurized CSF into the brain via a fluid pumping mechanism.

The spinal catheter 102 can include an elongated tubular portion 108 defining a central lumen 110 extending between a proximal end 112 operably coupled to the implantable pump 106 and a distal end 114 having an opening 116 positionable within the intrathecal space 62 of a patient, thereby enabling the spinal catheter 102 to draw a quantity of CSF from the intrathecal space 62 for reintroduction into other portions of the body of the patient.

The cranial catheter 104 can include an elongated tubular portion 118 defining a central lumen 120 extending between a proximal end 122 operably coupled to the implantable pump 106 and a distal end 124 operably coupled to a catheter tip 126. In some embodiments, the catheter tip 126 can include a blunt or rounded end 128 to minimize tissue disruption during insertion and location of the distal end 124 of the cranial catheter 104. Further, the tubular portion 118 can have an externally tapered distal end surface 130 to minimize tissue disruption during insertion.

In some embodiments, the catheter tip 126 can be constructed of a porous material to promote a more uniform and accurate dispersion of fluid into the cranial cavity of a patient. For example, in some embodiments, the catheter tip 126 can be constructed of a polysulfone hollow fiber, polyethylene, polyamide, polypropylene, expanded polytetrafluoroethylene, sintered microsphere material, or other porous or perforated material. In some embodiments, the catheter tip 126 can include a plurality of pores ranging in size between about 0.1-0.5 μm. In other embodiments, the catheter tip can be constructed of a perforated material, having between about 20-100 holes with a diameter of between about 0.001-0.005 inches. Other construction materials and pore or perforation sizes for the catheter tip 126 are also contemplated. Accordingly, in some embodiments, the catheter tip 126 can serve as a diffuser, thereby enabling a homogeneous delivery of fluid to the intraparenchymal space, or intra-cerebral ventricle space, or subarachnoid space surrounding the brain at an infusion rate of between about 0.1 μL/min and about 10 μL/min. In some embodiments, the catheter tip 126 can be configured to enable a homogeneous delivery of fluid at even higher infusion rates (e.g., 15 μL/min, 20 μL/min, etc.).

Figure 3:
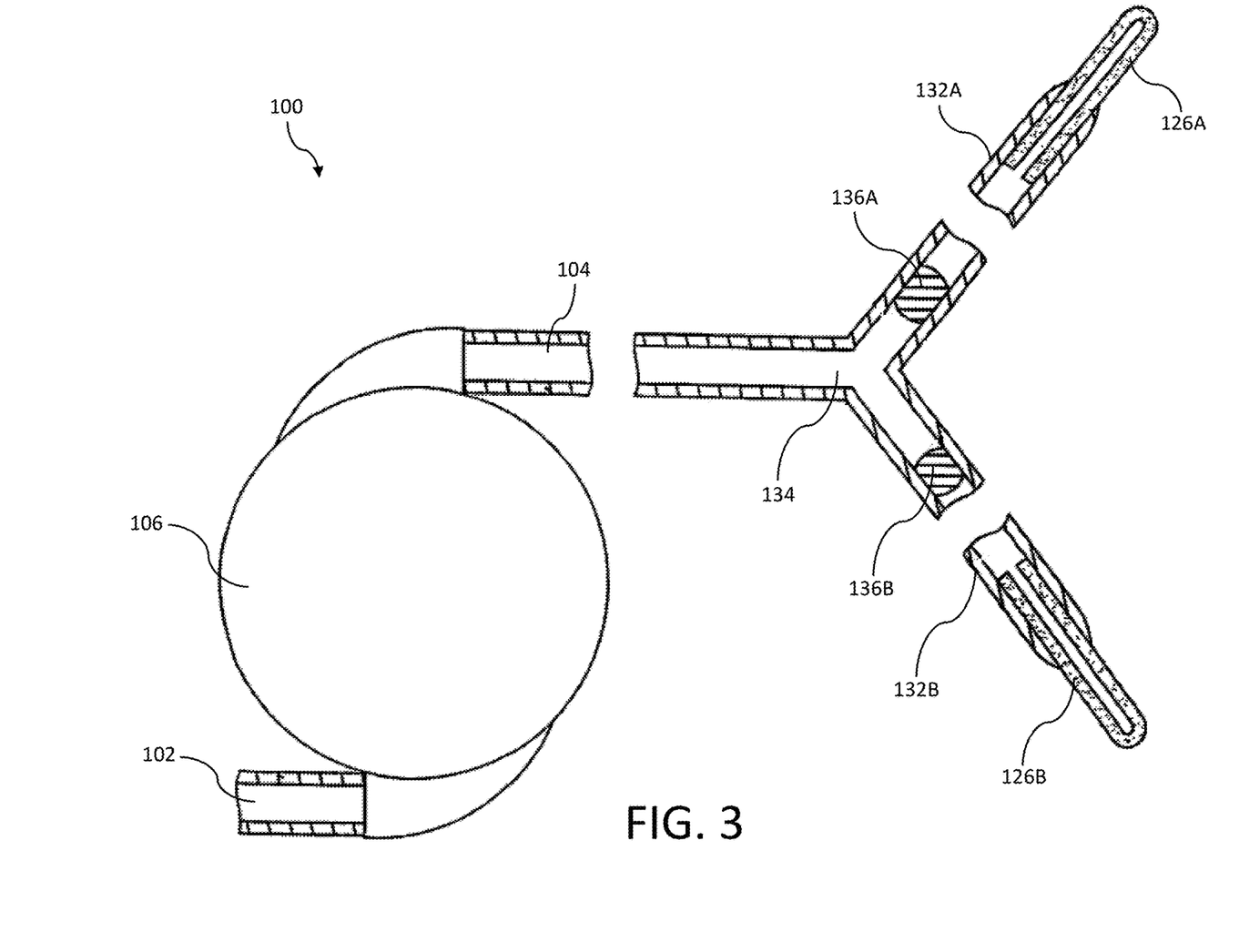
FIG. 3 depicts an implantable glymphatic pump having a bilateral intraparenchymal catheter arrangement, in accordance with an embodiment of the disclosure.
Figure 4:
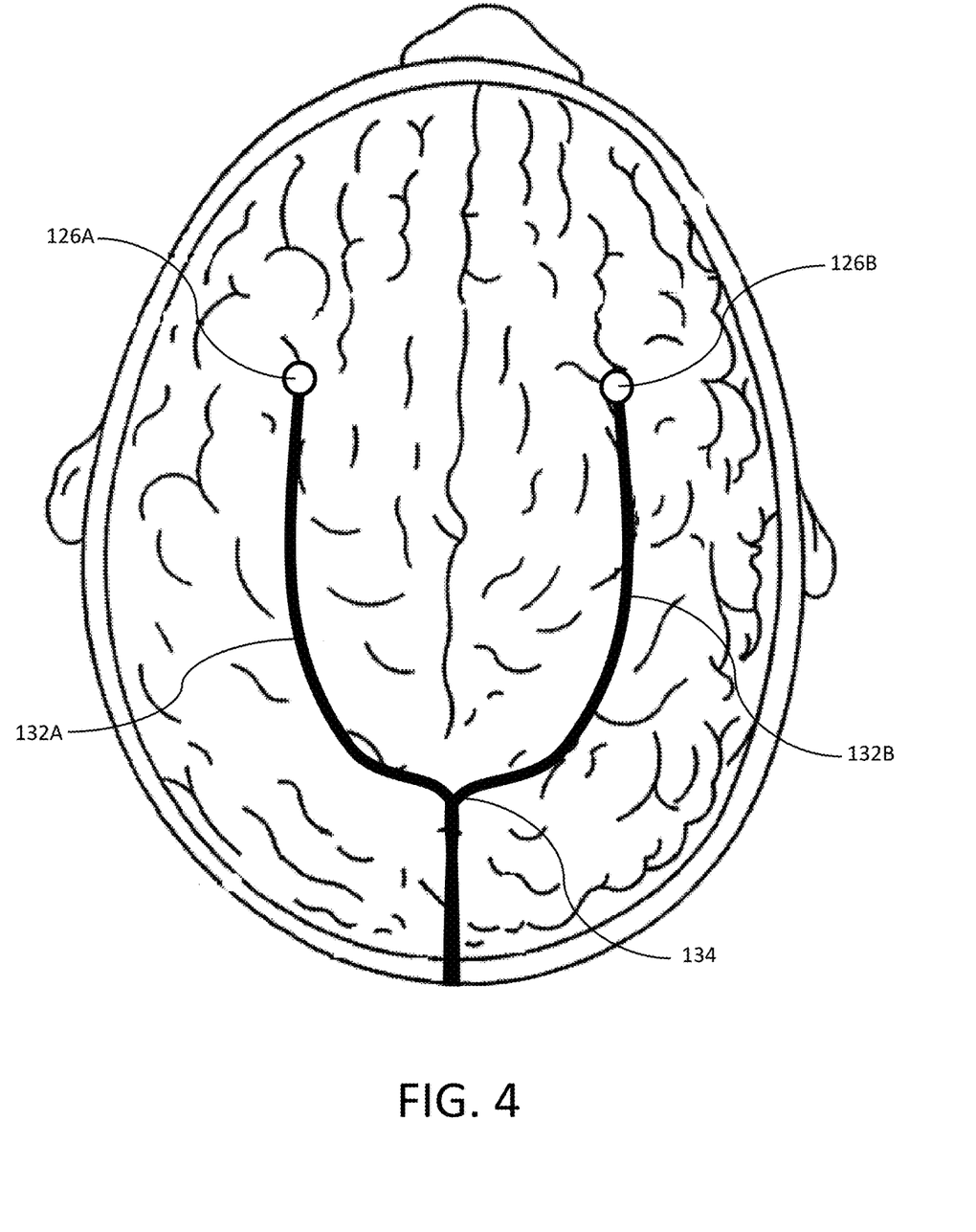
FIG. 4 depicts an implantable glymphatic pump having a bilateral intraparenchymal catheter arrangement implanted within a body of the patient, in accordance with an embodiment of the disclosure.

With additional reference to FIGS. 3-4, in some embodiments, the cranial catheter 104 can be adapted for bilateral delivery to both the left and right hemispheres of the brain to flush metabolites from parenchymal tissue. For example, in one embodiment, the cranial catheter 104 can include legs 132A/B, which can be positioned downstream of a connector 134. In such an embodiment, one or more restrictors 136A/B can be positioned in each of the legs 132A/B upstream of the catheter tips 126A/B to promote balanced flow between the legs 132A/B regardless of any variance in back pressure at the catheter tips 126A/B as a result of differing tissue densities at the CSF reintroduction site. Although FIG. 3-4 depict the cranial catheter 104 having two legs 132A/B, cranial catheters 104 having a greater number of legs (e.g., four legs, six legs, etc.) are also contemplated.

In some embodiments, the restrictors 136A/B can be constructed of a porous material, such as sintered metal, a porous polymer, or some other material suitable to establish a pressure drop to promote a more balanced flow between the legs 132A/B. In some embodiments, the restrictors 136 can be configured to establish a pressure drop of about 2-10 PSIG (e.g., with a flow rate of about 1-10 μL per minute) over the proximal end 122 and distal end 124 of each leg 132A/B. Where metals are used in the construction of either of the diffuser or restrictor, the metal can be any lightweight, high tensile strength material (e.g., tungsten, titanium or tantalum), preferably with nonmagnetic qualities suitable for use within a magnetic resonance imaging environment.

Figure 5A:
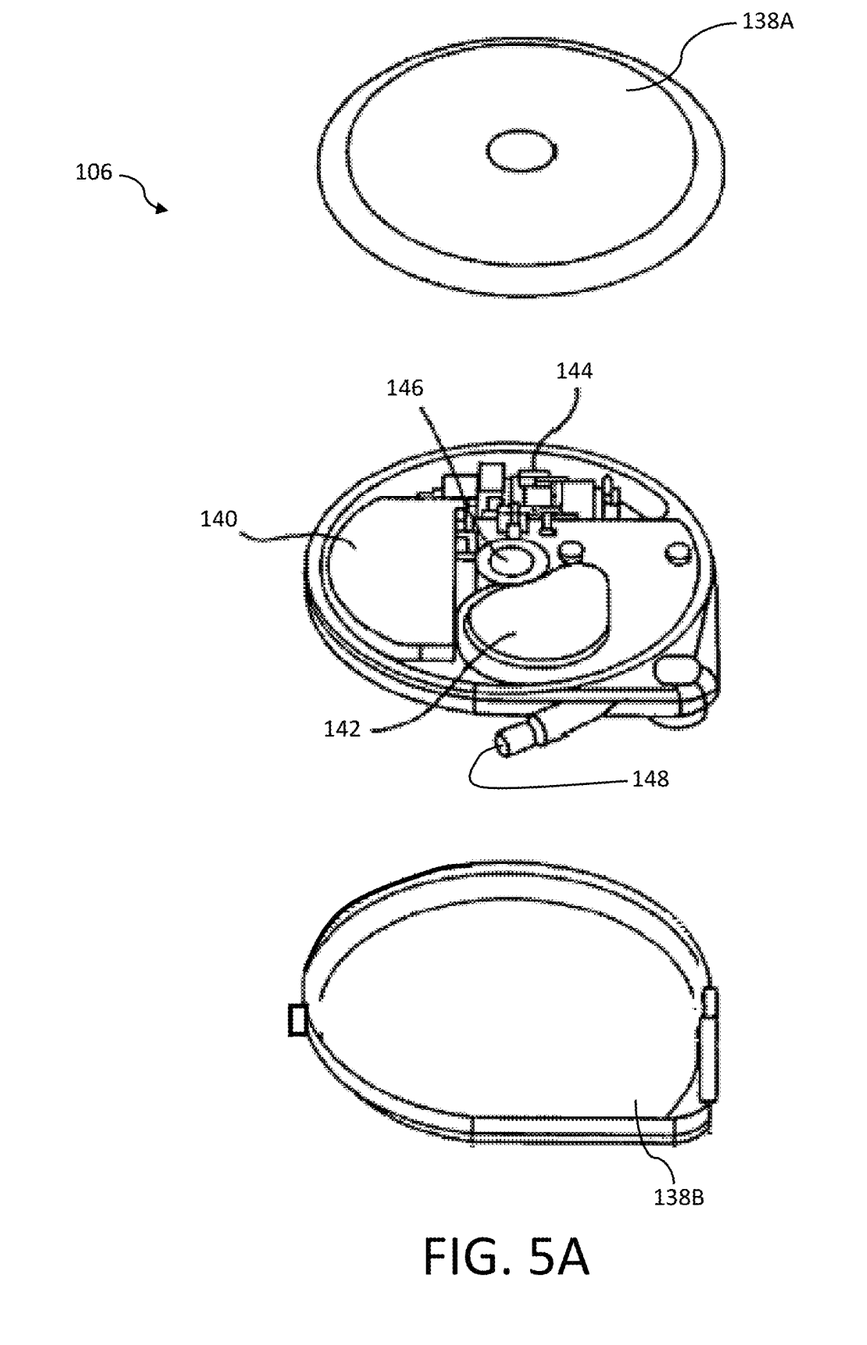
FIG. 5A is an exploded view depicting an implantable medical pump, in accordance with an embodiment of the disclosure.
Figure 5B:
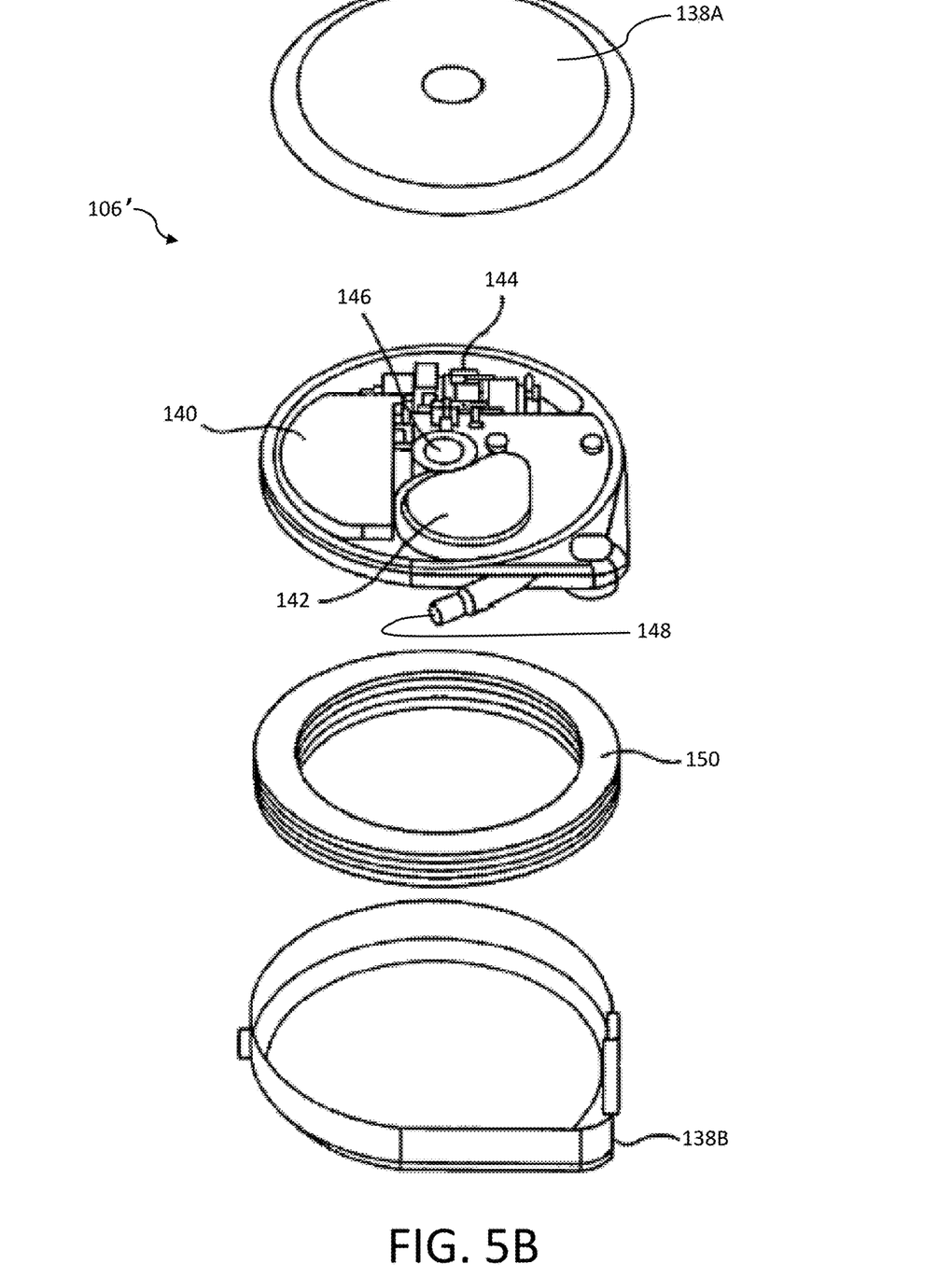
FIG. 5B is an exploded view depicting an implantable medical pump including a fluid reservoir, in accordance with an embodiment of the disclosure.

With reference to FIGS. 5A-B, exploded views of an implantable medical pump 106, 106' configured to draw CSF from the spine of a patient and reintroduce said CSF into the intracranial cavity of the patient for the purpose of flushing metabolites from parenchyma tissue, are depicted in accordance with embodiments of the disclosure. The implantable medical pump 106 can generally include a housing 138A/B, power source 140, fluid pump 142, and computing device 144. The housing 138, which can include an upper portion 138A and a lower portion 138B can be constructed of a material that is biocompatible and hermetically sealed, such as tungsten, titanium, tantalum, stainless steel, plastic, ceramic or the like.

An inlet port 146 operably coupled to the spinal catheter 102 can be configured to provide an inlet to CSF flowing into the fluid pump 142, and an outlet port 148 operably coupled to the cranial catheter 104 can be configured to provide an outlet to CSF flowing out of the fluid pump 142. As depicted in FIG. 5B, in some embodiments, the pump 106 can include a refillable fluid reservoir 150 carried by the housing 138 configured to contain a quantity of fluid. In such embodiments, the inlet port 146 can be fluidly coupled to the fluid reservoir 150, which can be fluidly coupled to the fluid pump 142.

Accordingly, in some embodiments, the fluid reservoir 150 can be configured to contain CSF or some other type of infusate for delivery into the cranial cavity of the patient. For example, in some embodiments, the fluid reservoir 150 can contain a saline solution or other type of cleansing solution configured to aid in flushing metabolites from the parenchymal tissue. In other embodiments, the fluid reservoir 150 can contain a medicament helpful in generally increasing the porosity of the parenchymal tissue. For example, in some embodiments, the medicament can be a flow modulator, such as VEGFR3 agonist or Fibroblast Growth Factor 2 (FGF2); although other medicaments are also contemplated. In yet other embodiments, the fluid reservoir 150 can be utilized as a CSF reserve, thereby enabling improved regulation of intracranial and intrathecal space pressures. In such embodiments, infusate or medicament from the fluid reservoir 150 can optionally be mixed with CSF drawn from the intrathecal space for reintroduction into the parenchyma.

Embodiments having a fluid reservoir 150 can have a displacement volume of approximately 120 cc or less. Alternatively, embodiments without a fluid reservoir 150 (which can account for approximately 80% of the volume of an implantable pump 106) can have a displacement volume of 60 cc or less; although other displacement volumes, such as 50 cc or less, 40 cc or less, 35 cc or less, 30 cc or less, and 25 cc or less are also contemplated. Accordingly, embodiments of the present disclosure can enable the inclusion of a much smaller implantable pump than conventional implantable infusion pumps, enabling the implantation of a less intrusive, smaller, more compact, lighter weight device.

Figure 6:
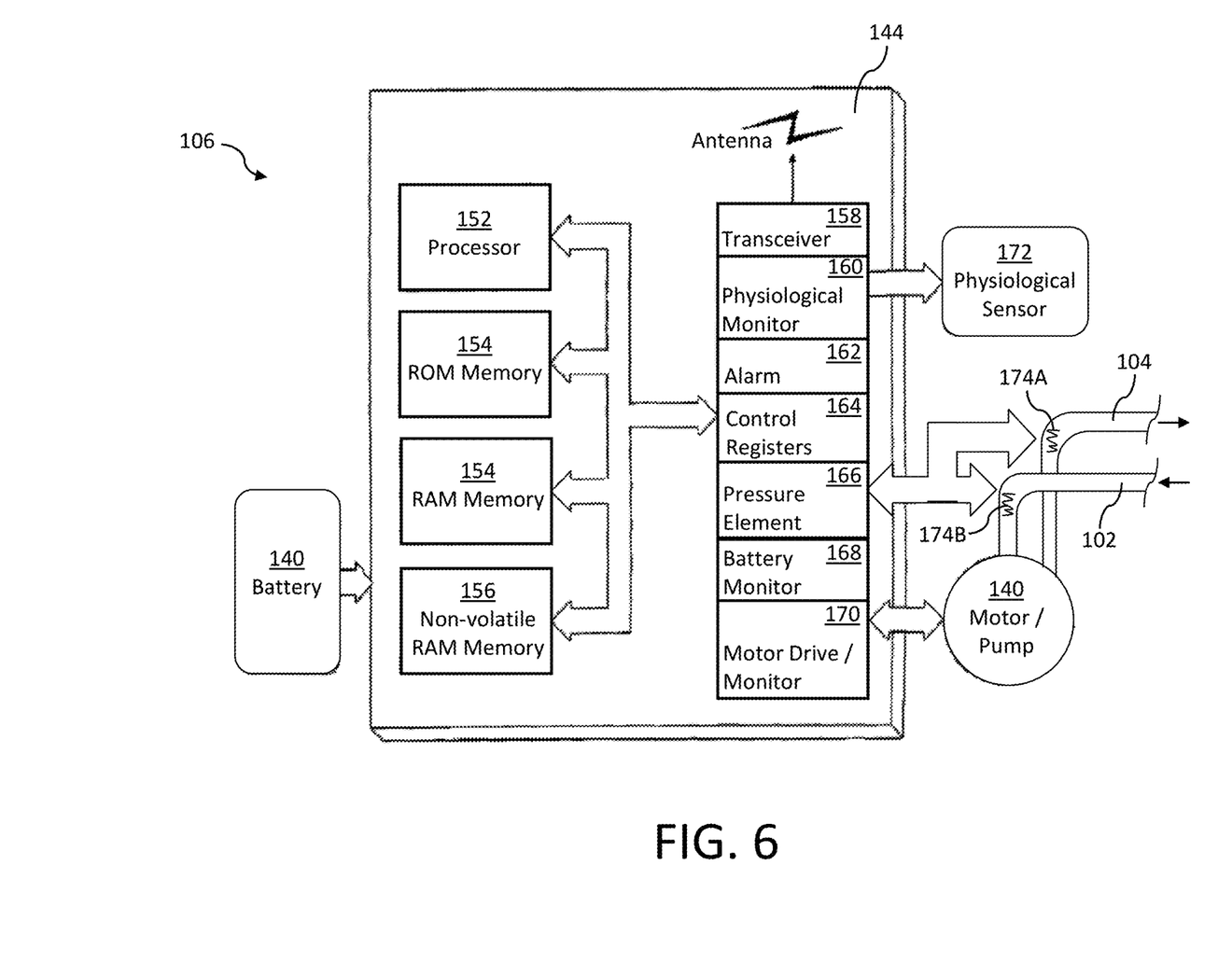
FIG. 6 is a block diagram depicting an implantable medical pump, in accordance with an embodiment of the disclosure.

Referring to FIG. 6, a block diagram of an implantable pump 106 configured to draw CSF from the spine of a patient and reintroduce said CSF into the intracranial cavity of the patient for the purpose of flushing metabolites from parenchymal tissue, is depicted in accordance with an embodiment of the disclosure. The power source 140 can be configured to provide power to the fluid pump 142 and computing device 144. The power source 140, which can be a battery such as a lithium-ion battery, can be monitored via the battery monitor 158. Control of the fluid pump 142 can be directed by a motor drive/monitor element 170.

The computing device 144 can include a processor 152, memory 154/156, and transceiver circuitry 158. In one embodiment, the processor 152 can be a microprocessor, logic circuit, application specific integrated circuit (ASIC) state machine, gate array, controller, or the like. The computing device 140 can generally be configured to control a flow of fluid through fluid pump 142. In some embodiments, programmed parameters or specific treatment protocols can be stored in the memory 154/156 for specific implementation by one or more control registers 164. In one embodiment, the control register 164 can be a processor register configured to controls the general behavior of processor 154. Functions performed by the control register 164 can include interrupt control, switching the addressing mode, and coprocessor control, among other functions.

In some embodiments, at least one of an upstream pressure (e.g., fluid pressure within the spinal catheter 102) or downstream pressure (e.g., fluid pressure within the cranial catheter 104) can be monitored via an optional pressure element 166. In embodiments including the pressure element 166, the implantable glymphatic pump 100 can be configured to detect abnormal pressure conditions during operation of the fluid pump 142, including a determination when a flow of CSF may be too aggressive for the current porosity of the parenchymal tissue. For example, the pressure element 166 can be configured to determine a downstream back pressure or a ratio between a downstream pressure and upstream pressure, which can be compared to one or more defined limits or range of defined limits. One or more safety responses can be triggered when the sensed pressures exceed the defined limits, including reducing fluid pump 142 speed to decrease the flow rate until the sensed pressures fall within an acceptable range of defined limits.

Figure 8:
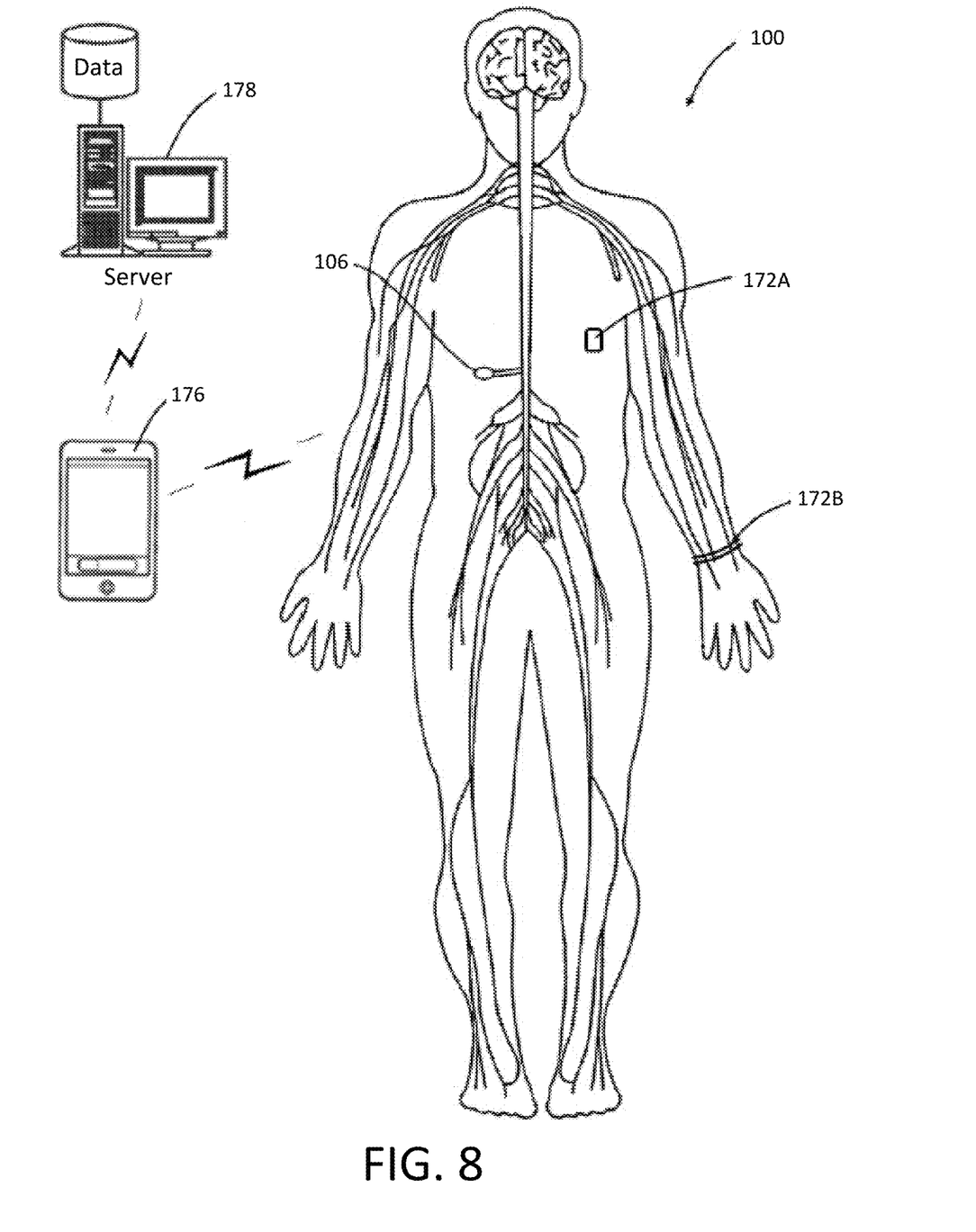
FIG. 8 depicts an implantable glymphatic pump configured to monitor one or more physiological conditions of a patient to infer parenchymal tissue porosity for improved flushing of metabolites from the parenchyma, in accordance with an embodiment of the disclosure.

The transceiver circuitry 158 can be configured to receive information from and transmit information to an external programmer 176 or server 178 (as depicted in FIG. 8). An alarm 162 can be configured to activate one or more notification, alert or alarm features, such as an illuminated, auditory or vibratory alarm.

In some embodiments, the pressure element 166 can include an upstream pressure sensor 174A and a downstream pressure sensor 174B, which can be configured to respectively monitor upstream (e.g., pump inlet) and downstream (e.g. pump outlet) pressures. The pressure sensors 174A/B can be carried by the housing 138 or can be coupled to the respective cranial and spinal catheters 104/102. For example, in one embodiment, the pressure sensors 174A/B can be strain gauges configured to detect a deformation in channels through which CSF is flowing; although other types of pressure sensors 174 are also contemplated.

In some embodiments, one or more notifications, alerts or alarms (e.g., via alarm 162) can be triggered by the sensed pressure or pressure ratio exceeding a defined threshold or acceptable range of defined threshold values stored in memory 154/156 and/or transmitted from an external device 176/178. Alternatively, or in addition to the notifications, alerts and alarms, sensed pressures falling outside of the defined limits or ranges can be logged in the memory 154/156 for later review by a clinician and/or transmitted to an external device 176/178.

Figure 7:
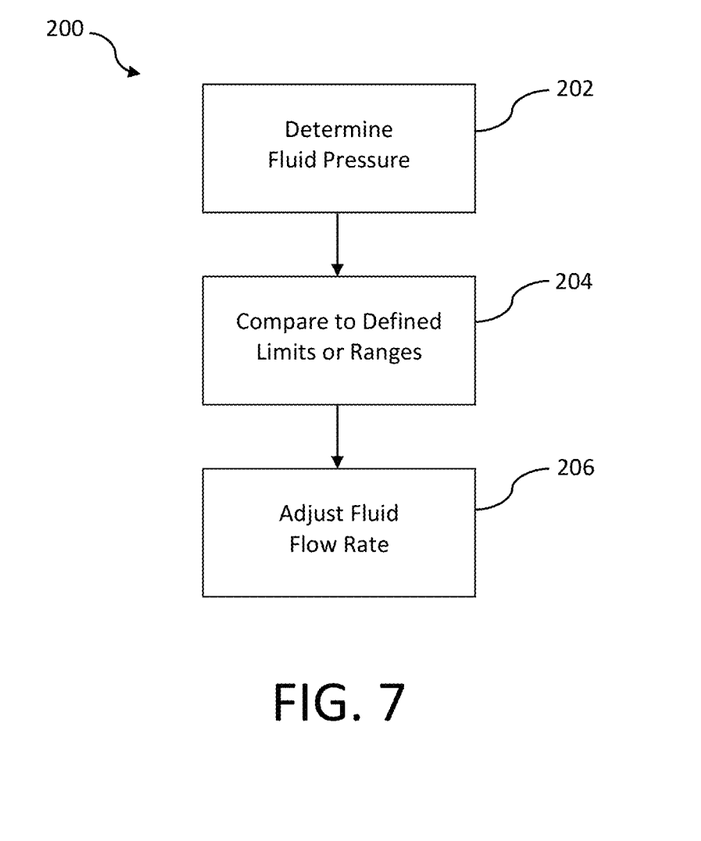
FIG. 7 is a flowchart depicting a method of determining when a flow a CSF may be too aggressive for a current porosity of parenchymal tissue, in accordance with an embodiment of the disclosure.

With additional reference to FIG. 7, a method 200 to be performed by computing device 144 of determining when a flow of CSF may be too aggressive for a current porosity of parenchymal tissue is depicted in accordance with an embodiment of the disclosure. At 202, data from the one or more pressure sensors 174A/B can be received by the pressure element 166. In some embodiments, the downstream pressure (e.g., sensed by pressure sensor 174A) can be divided by the upstream pressure (e.g., sensed by pressure sensor 174B) to establish a pressure ratio. Other computational functions and processing involving data from the pressure sensors 174A/B is also contemplated.

At 204, the received pressure data can be compared by computing device 144 or processor 152 to one or more limits stored in memory 154/156 as an aid in determining whether the associated measured pressures may exceed a defined threshold stored in memory 154/156, thereby indicating the presence of a potential safety hazard to the patient (e.g., an overly aggressive CSF flow rate). Conversely, received pressure data below a defined range may indicate a less than optimal flow of CSF for the current porosity of the parenchymal tissue. For example, in one embodiment, the defined limits for an acceptable downstream pressure can be in the range of between about 3-5.5 PSIG, with 5.5 PSIG representing an upper safety threshold. In one embodiment, the defined limits for an acceptable downstream/upstream pressure ratio can be between about 1.5-8.0. These limits represent one example embodiment and should not be considered limiting; the use of other limits, ranges of pressures and ratios is also contemplated.

At 206, feedback can be provided to the motor drive/monitor 170 to adjust a rate of fluid flow provided by the fluid pump 142. For example, where sensed pressures or ratios exceed an upper safety threshold, the speed of the fluid pump 142 can be stepped down, decreased, or stopped altogether to ensure patient safety. Conversely, where the sensed pressures or ratios fall below the defined range, the speed of the fluid pump 142 can be increased to promote a greater flow of CSF fluid. Thereafter, computing device 144 can repeat method 200 to ensure patient safety and continually seek to optimize the therapy by matching the CSF flow rate to the current porosity of the parenchymal tissue.

With continued reference to FIG. 6, in some embodiments, the implantable glymphatic pump 100 can include a physiological monitor 160 configured to monitor one or more physiological conditions of a patient, which may influence successful flushing of metabolites from the brain parenchyma. Increased CSF flow rates within a patient's natural, biological glymphatic system is a dynamic phenomenon closely correlated with a patient's arterial pulse wave; although other factors, such as respiratory waves, the patient's posture, jugular venous pressure, and physical effort may also affect cerebrospinal flow dynamics and pressure. Porosity of the parenchymal tissue is believed to be closely associated with sleep and wake cycles, whereby the parenchymal tissue generally becomes more porous during sleep (e.g., pore dilation increases between 20-50%), thereby enabling a greater CSF flow rate through the parenchymal tissue, which facilitates an increased rate in flushing of metabolites.

The physiological monitor 160 can include one or more physiological sensors 172 can be configured to monitor one or more physiological conditions which may have a direct or indirect effect on parenchymal tissue porosity. Examples of physiological sensors 172 can include a heart rate monitor, pulse oximeter, respiratory sensor, perspiration sensor, posture orientation sensor, motion sensor, accelerometer, temperature sensor, or the like. In some embodiments, a decrease in patient activity (as measured by a decrease in heart rate, respiratory rate, etc.) can infer an increase in porosity of the parenchymal tissue.

Based on an inferred increase in porosity of the parenchymal tissue, which in some cases can be confirmed by the pressure element 166, feedback can be provided to the motor drive/monitor 170 to adjust the rate of fluid flow provided by the fluid pump 142 to optimize the therapy by increasing the CSF flow rate to the inferred porosity of the parenchymal tissue. Conversely, an increase in patient activity, indicating wakefulness, can be followed by an adjustment of the pump 142 to decrease the CSF fluid flow rate.

Referring to FIG. 8, an implantable glymphatic pump 100 configured to monitor one or more physiological conditions of the patient to infer parenchymal tissue porosity for improved flushing of metabolites from the parenchyma, is depicted in accordance with an embodiment of the disclosure. In some embodiments, the one or more physiological sensors 172 can be carried in the housing 138 of the implantable pump 106. In other embodiments, the one or more physiological sensors 172A/B can be worn by a patient (e.g., a smart watch, wristband tracker, sensors embedded in clothing, etc.) carried by the patient (e.g., a smart phone, mobile computing device, etc.) or positioned in proximity to the patient (e.g., a stationary monitor, etc.). In some embodiments, conditions sensed by the one or more sensors 172 can be communicated to a mobile computing device 176 or server 178. In other embodiments, the one or more sensors 172 can communicate directly with the implantable pump 106.

Figure 9:
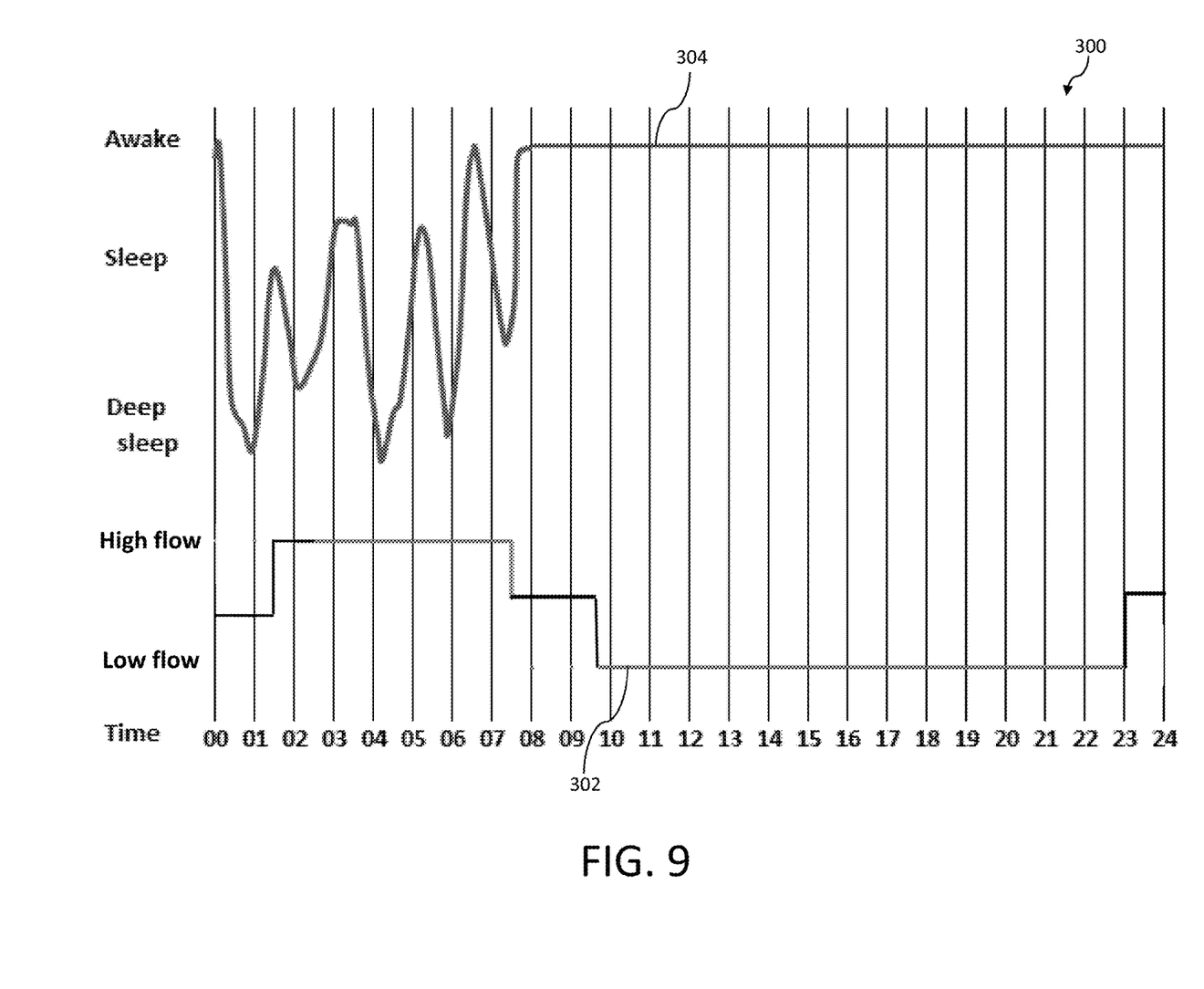
FIG. 9 is a graphical depiction of manipulated CSF flow rates according to a patient's sleep cycle, in accordance with an embodiment of the disclosure.

Referring to FIG. 9, a graph 300 showing control of CSF flow rates 302 through the parenchymal tissue according to a patient's sleep cycle 304 is depicted in accordance with an embodiment of the disclosure. In some embodiments, data from the one or more physiological sensors 172 can be utilized to analyze a patient's sleep cycle 304. In some embodiments, either of the implantable pump 106 or mobile computing device 176 (as depicted in FIG. 8) can be configured to learn daily routines and sleep patterns of the patient over the course of several days. A speed of the fluid pump 142 can be modulated according to the patient's sleep cycle, including increasing CSF flow rates during times when the patient is perceived to be asleep and decreasing CSF flow rates during wakefulness to correspond with physiological changes in the porosity of the parenchymal tissue.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:
1. An implantable glymphatic pump comprising:
at least one spinal catheter having a first distal end configured to be positioned within an intrathecal space of a spine of a patient;
at least one intraparenchymal catheter having a second distal end configured to be positioned within a parenchymal tissue of the patient; and
an implantable pump configured to draw cerebrospinal fluid from the intrathecal space of the spine in the patient via the at least one spinal catheter, and reintroduce the cerebrospinal fluid to the parenchymal tissue of the patient via the at least one intraparenchymal catheter to encourage a flow of the cerebrospinal fluid through the parenchymal tissue, wherein the implantable pump includes at least one physiological sensor configured to aid in a determination of a preferred operating time of the implantable pump, and wherein the preferred operating time of the implantable pump occurs during a sleep state of the patient.

2. The implantable glymphatic pump of claim 1, wherein the at least one intraparenchymal catheter includes a first intraparenchymal catheter configured to be positioned in a right hemisphere of a brain of the patient and a second intraparenchymal catheter configured to be positioned in a left hemisphere of the brain of the patient.

3. The implantable glymphatic pump of claim 1, wherein the implantable pump comprises a peristaltic pump, a diaphragm pump, a piston pump, a rotor pump, or a screw pump.

4. The implantable glymphatic pump of claim 1, wherein the implantable pump includes a fluid reservoir.

5. The implantable glymphatic pump of claim 4, wherein the implantable pump is further configured to mix an infusate contained in the fluid reservoir with the cerebrospinal fluid for introduction into the parenchymal tissue of the patient.

6. The implantable glymphatic pump of claim 1, wherein the at least one physiological sensor comprises a heart rate sensor, a respiratory sensor, an inclination sensor, an accelerometer, or a temperature sensor.

7. The implantable glymphatic pump of claim 1, wherein the implantable pump includes at least one pressure sensor configured to sense a pressure of the cerebrospinal fluid reintroduced into the parenchymal tissue.

8. The implantable glymphatic pump of claim 7, wherein the implantable pump further includes a processor configured to use data sensed by the at least one pressure sensor to infer a porosity of the parenchymal tissue as an aid in regulating a flow rate of the implantable pump.

9. The implantable glymphatic pump of claim 1, wherein the implantable pump is configured to infuse the cerebrospinal fluid to the parenchymal tissue of the patient via the at least one intraparenchymal catheter at a rate of between about 0.1 µL/min and about 20 µL/min.

10. The implantable glymphatic pump of claim 1, wherein the implantable pump occupies a total volume of about 60 mL or less.

11. An implantable glymphatic pump comprising:
at least one spinal catheter having a distal end configured to be positioned within an intrathecal space of a spine of a patient;
at least one cranial catheter having a distal end distal end configured to be positioned within a cranial cavity of the patient; and
an implantable pump configured to draw cerebrospinal fluid from the intrathecal space of the spine in the patient via the at least one spinal catheter, and reintroduce said cerebrospinal fluid to the cranial cavity of the patient via the one or more cranial catheters to encourage a flow of the cerebrospinal fluid through a brain parenchyma of the patient, wherein the implantable pump includes at least one physiological sensor configured to aid in a determination of a preferred operating time of the implantable pump, wherein the preferred operating time of the implantable pump occurs during a sleep state of the patient.

12. The implantable glymphatic pump of claim 11, wherein the at least one physiological sensor comprises a heart rate sensor, a respiratory sensor, an inclination sensor, an accelerometer, or a temperature sensor.

13. The implantable glymphatic pump of claim 11, wherein the implantable pump comprises a peristaltic pump, a diaphragm pump, a piston pump, a rotor pump, or a screw pump.

14. The implantable glymphatic pump of claim 11, wherein the implantable pump occupies a total volume of about 60 mL or less.

15. The implantable glymphatic pump of claim 11, wherein the at least one cranial catheter is configured reintroduce the cerebrospinal fluid directly into the brain parenchyma.

16. The implantable glymphatic pump of claim 11, wherein the at least one cranial catheter includes a first cranial catheter configured to be positioned in a right hemisphere of a brain of the patient and a second catheter configured to be positioned in a left hemisphere of the brain of the patient.

17. The implantable glymphatic pump of claim 11, wherein the implantable pump includes a pressure sensor configured to sense a pressure of cerebrospinal fluid reintroduced into the cranial cavity.

18. The implantable glymphatic pump of claim 11, wherein the implantable pump is configured to infuse the cerebrospinal fluid to the cranial cavity of the patient via the at least one cranial catheter at a rate of between about 0.1 µL/min and about 20 µL/min.

19. The implantable glymphatic pump of claim 17, wherein the implantable pump further includes a processor configured to use data sensed by the pressure sensor to infer a porosity of the brain parenchyma as an aid in regulating a flow rate of the implantable pump.

20. An implantable glymphatic pump comprising:
at least one spinal catheter having a first distal end configured to be positioned within an intrathecal space of a spine of a patient;
at least one cranial catheter having a second distal end configured to be positioned within a cranial cavity of the patient;
an implantable pump configured to draw cerebrospinal fluid from the intrathecal space of the spine in the patient via the at least one spinal catheter, and reintroduce said cerebrospinal fluid to the cranial cavity of the patient via the one or more cranial catheters to encourage a flow of the cerebrospinal fluid through a brain parenchyma of the patient, wherein the implantable pump includes a pressure sensor configured to sense a pressure of the cerebrospinal fluid reintroduced into the cranial cavity; and
a processor configured to use data sensed by the pressure sensor to infer a porosity of the brain parenchyma as an aid in regulating a flow rate of the implantable pump.

21. The implantable glymphatic pump of claim 20, wherein the implantable pump comprises a peristaltic pump, a diaphragm pump, a piston pump, a rotor pump, or a screw pump.

22. The implantable glymphatic pump of claim 20, wherein the implantable pump occupies a total volume of about 60 mL or less.

23. The implantable glymphatic pump of claim 20, wherein the at least one cranial catheter is configured reintroduce the cerebrospinal fluid directly into the brain parenchyma.

24. The implantable glymphatic pump of claim 20, wherein the at least one cranial catheter includes a first cranial catheter configured to be positioned in a right hemisphere of a brain of the patient and a second catheter configured to be positioned in a left hemisphere of the brain of the patient.

25. The implantable glymphatic pump of claim 20, wherein the implantable pump includes at least one physiological sensor configured to aid in a determination of a preferred operating time of the implantable pump.

26. The implantable glymphatic pump of claim 25, wherein the preferred operating time of the implantable pump occurs during a sleep state of the patient.

27. The implantable glymphatic pump of claim 25, wherein the at least one physiological sensor comprises a heart rate sensor, a respiratory sensor, an inclination sensor, an accelerometer, or a temperature sensor.

28. A method of aiding a glymphatic system of a patient comprising:
   drawing cerebrospinal fluid with an implantable pump from an intrathecal space of a spine of the patient;
   pumping the cerebrospinal fluid through the implantable pump;
   reintroducing the cerebrospinal fluid into a brain parenchyma of the patient with the implantable pump to encourage a flow of the cerebrospinal fluid through the brain parenchyma as an aid in flushing metabolites from the brain parenchyma of the patient;
   sensing, via a pressure sensor, a pressure of the cerebrospinal fluid reintroduced into the brain parenchyma; and
   inferring a porosity of the brain parenchyma from data sensed by the pressure sensor.

29. The method of claim 28, further comprising mixing an infusate contained in a fluid reservoir of the implantable pump with said cerebrospinal fluid prior to reintroduction of said cerebrospinal fluid into the brain parenchyma.

30. The method of claim 28, further comprising determining a preferred operating time of the implantable pump via feedback from at least one physiological sensor.

31. The method of claim 30, wherein the preferred operating time of the implantable pump occurs during a sleep state of the patient.

* * * * *